(12) United States Patent
Lai

(10) Patent No.: US 9,738,889 B2
(45) Date of Patent: Aug. 22, 2017

(54) RAPID NUCLEIC ACID EXTRACTION METHOD AND APPARATUS

(71) Applicant: Daniel Lai, Auckland (NZ)

(72) Inventor: Daniel Lai, Auckland (NZ)

( * ) Notice: Subject to any disclaimer, the term of this patent is extended or adjusted under 35 U.S.C. 154(b) by 78 days.

(21) Appl. No.: 14/830,210

(22) Filed: Aug. 19, 2015

(65) Prior Publication Data

US 2016/0108393 A1    Apr. 21, 2016

Related U.S. Application Data

(62) Division of application No. 14/517,527, filed on Oct. 17, 2014, now Pat. No. 9,145,581.

(51) Int. Cl.
  *C12Q 1/68* (2006.01)
  *C12N 15/10* (2006.01)
  *B01L 3/00* (2006.01)

(52) U.S. Cl.
  CPC .......... *C12N 15/1017* (2013.01); *B01L 3/502* (2013.01); *B01L 3/523* (2013.01); *C12Q 1/6806* (2013.01); *B01L 2300/047* (2013.01); *B01L 2300/0672* (2013.01); *B01L 2400/0478* (2013.01)

(58) Field of Classification Search
  CPC ................ B01L 2200/10; B01L 3/502; B01L 2300/087; B01L 2200/16; B01L 2400/0481; B01L 2300/0672; B01L 3/5023; B01L 2400/0478; B01L 2400/0683; B01L 2200/0631; B01L 2300/044; B01L 3/565; B01L 2200/0621; B01L 2300/0832; B01L 2200/0605; C12Q 1/6806; C12Q 1/6834
  See application file for complete search history.

(56) References Cited

U.S. PATENT DOCUMENTS

| 6,251,660 B1 * | 6/2001 | Muir ................. B01L 3/502 422/236 |
| 2004/0126783 A1 * | 7/2004 | Bortolin ............. B01L 3/502 435/6.12 |
| 2004/0161788 A1 * | 8/2004 | Chen ................. B01L 3/502 435/6.11 |
| 2015/0024384 A1 * | 1/2015 | Peyvan ............... B01J 4/02 435/6.1 |

* cited by examiner

*Primary Examiner* — Sally Merkling
(74) *Attorney, Agent, or Firm* — Lapple Ubell IP Law, LLP; Franklin D. Ubell

(57) ABSTRACT

A syringe device having a plunger beneath which is disposed a rupturable capsule containing a nucleic acid wash buffer and a rupturing mechanism for rupturing the capsule, wherein the capsule, syringe, plunger, and rupturing mechanism are so configured as to first apply pneumatic pressure to force a nucleic acid solution through a membrane and to thereafter rupture the capsule and force a first volume of the wash buffer through the membrane.

16 Claims, 7 Drawing Sheets

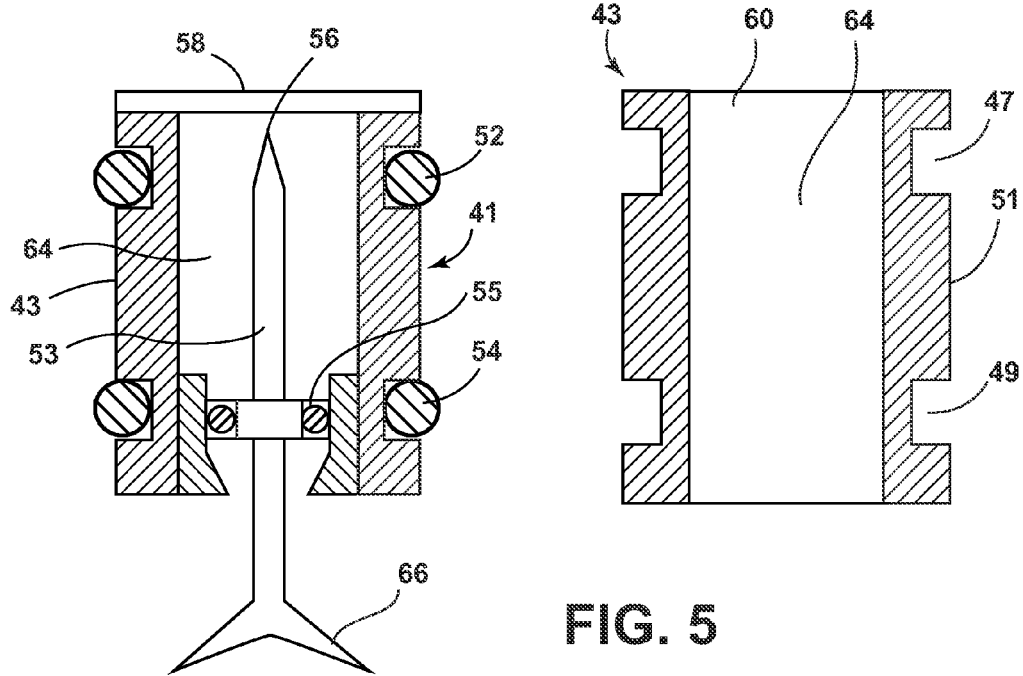
FIG. 4
FIG. 5
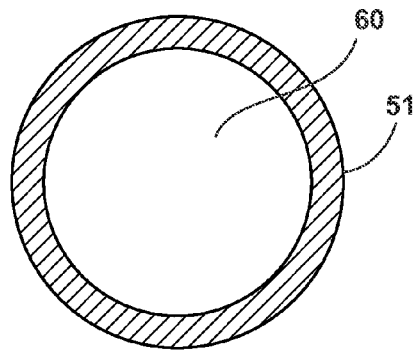
FIG. 6
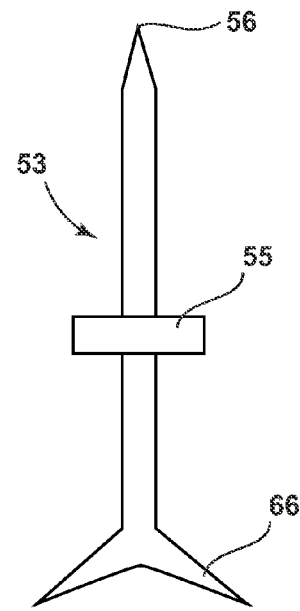
FIG. 7

RAPID NUCLEIC ACID EXTRACTION METHOD AND APPARATUS

CROSS REFERENCE TO RELATED APPLICATIONS

This application is a divisional of and claims priority to U.S. Utility patent application Ser. No. 14/517,527, entitled "Rapid Nucleic Acid Extraction Method And Apparatus," filed on Oct. 17, 2014, the contents of which is incorporated herein by reference in its entirety.

BACKGROUND OF THE DISCLOSURE

Field of the Disclosure

The present disclosure relates to extraction of nucleic acid and in particular to the extraction of nucleic acid via an extraction device or apparatus.

Related Art

Nucleic acids are polymeric macromolecules essential for all known life forms. Nucleic acids include DNA (Deoxyribonucleic Acid) and RNA (Ribonucleic Acid) made from monomers known as nucleotides. The most important macromolecules found in living things are nucleic acids and proteins, as they function in encoding, transmitting and expressing genetic information. To examine nucleic acid, an 'extraction' process is required. Other names for "extraction" include "purification", "isolation", or "concentration". Complex laboratory methods for extraction of nucleic acid are known such as extraction via column chromatography and magnetic beads based separation.

SUMMARY

According to illustrative embodiments, a new method for nucleic acid extraction is provided which enables fast, reliable and portable tests. Various illustrative embodiments provide a new platform for fast, on-site nucleic acid extraction without the need for expensive instruments and/or specialized laboratory environment.

According to one embodiment, the processes of binding, washing and eluting of nucleic acid material involved in the extraction of nucleic acid are incorporated within the extraction apparatus, which applies the buffers and/or solutions required for nucleic acid extraction.

According to one illustrative embodiment, a first container is configured to receive a nucleic acid solution ready for extraction. The first container has a membrane located at a lower end thereof, which is configured to capture nucleic acid while passing other components of the solution. The first container is disposed above a waste collection container configured to receive the lower end of the first container.

Further according to the illustrative embodiment, a syringe is insertable into an open top end of the first container and contains a capsule having a chamber filled with a wash buffer solution, which is moveable downwardly in response to activation of a plunger of the syringe. The capsule further has a seal across a top opening thereof and a spike mounted in a lower end thereof, the spike having a first end extending out of a lower end of the capsule and a second end extending into the chamber.

In one embodiment, the capsule is so configured and positioned within the syringe such that downward movement of the capsule within the syringe will first force the nucleic acid solution in the first container through the membrane, after which the spike contacts a lower surface of the syringe and stops while the capsule continues to move downwardly, causing the spike to break or rupture the seal, thereby releasing the wash buffer solution into the syringe. Further downward movement of the syringe forces the wash buffer solution through the membrane, thereby resulting in pure nucleic acid residing on the membrane. The apparatus may further comprise a second syringe apparatus configured to further wash the membrane of the first container to elute either RNA or DNA or other selected nucleic acid.

BRIEF DESCRIPTION OF THE DRAWINGS

FIG. 4 is a side sectional view of an illustrative wash buffer capsule;

FIG. 5 is a side sectional view of a body component of the capsule of FIG. 4;

FIG. 6 is a top view of the capsule of FIG. 4;

FIG. 7 is a side view of a spike component of the capsule of FIG. 4;

DETAILED DESCRIPTION

Figure 1:
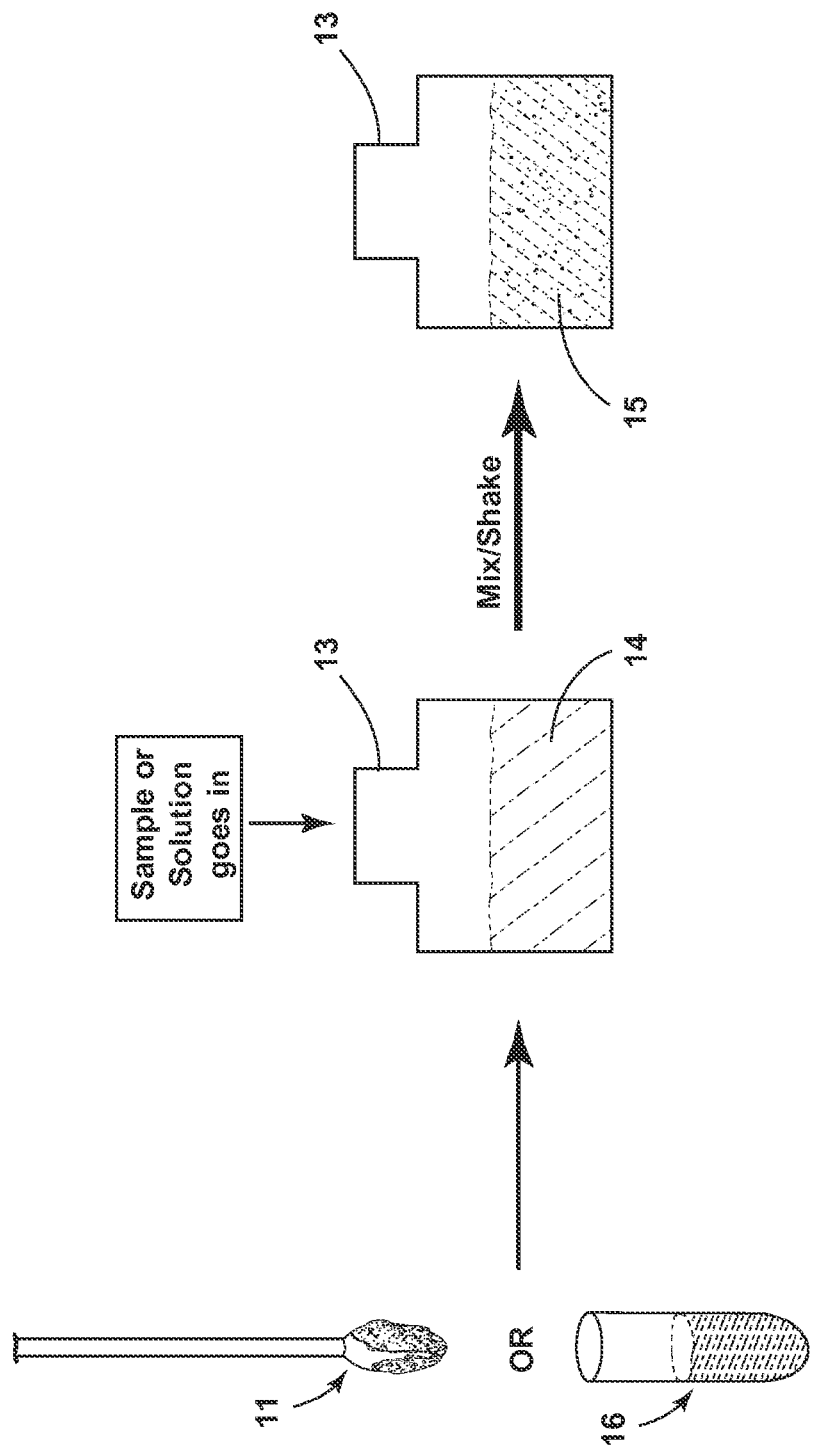
FIG. 1 is a schematic diagram of steps of an illustrative nucleic acid solution preparation procedure.

In an illustrative embodiment, according to FIG. 1, a sample 11 or solution 16, for example, human saliva on a cotton swab, body fluids such as blood, sweat, or urine, skin, hair, plant samples, cell cultures, microorganism cultures, soil, or any sample that potentially comprises nucleic acids, is supplied to a container 13, which is pre-filled with a nucleic acid preparation solution 14 containing appropriate pH buffers and other additives to break open cells of the sample to release nucleic acid and to preserve the nucleic acid by, for example, preventing enzymes from degrading the nucleic acid. The additives may comprise detergents, chelating agents, salts, chaotropic agents, solvents such as ethanol and isopropanol, acids, bases, with optional protease, DNAse or RNAse. In one embodiment, the preparation solution 14 functions as a diluter and pH adjuster. The container 13 is then subjected to a mixing/shaking step, which results in a nucleic acid solution 15 ready for purification/extraction.

Figure 2:
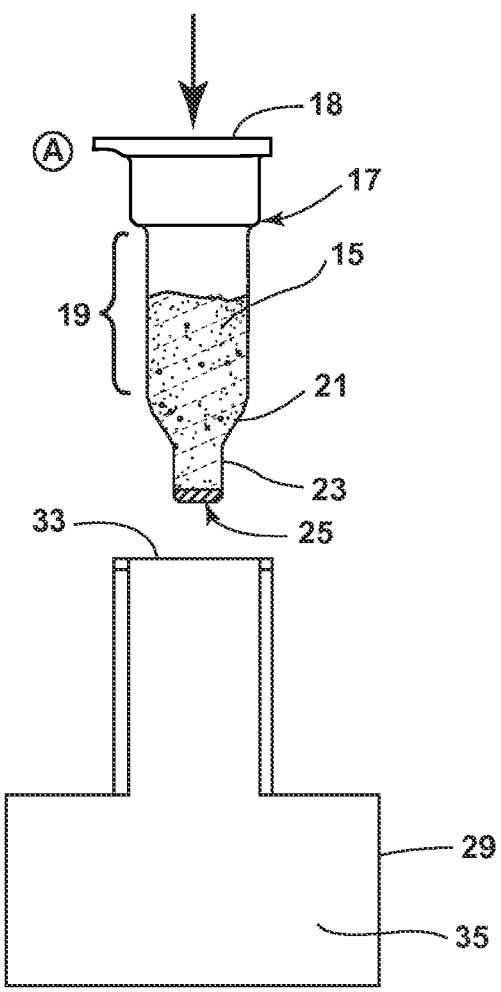
FIG. 2 is a side view illustrating further steps and apparatus employed in an illustrative nucleic acid extraction process.

As illustrated in FIG. 2, a vial or first container 17 is then filled with a selected amount of the solution 15. In one embodiment, the vial 17 may have a cylindrical upper segment 19 and a conically tapered portion 21 forming into a cylindrical nozzle 23 which is of a smaller diameter than that of the cylindrical segment 19 and is filled with a membrane 25. The contents of the vial 17 may be referred to as a nucleic acid binding column, and the membrane 25 functions to retain the nucleic acid in the solution 15 while undesired components are washed through the membrane 25. In one embodiment, the membrane 25 may be silica based. Many ways to fabricate a membrane 25 are known to those skilled in the art. In various embodiments, the membrane may comprise silica ($SiO_2$), silicon oxide(s), glass powder, alkyl silica, aluminum silicate (zeolite), activated silica with —$NH_2$, or a mix including any number of the above.

Figure 3:
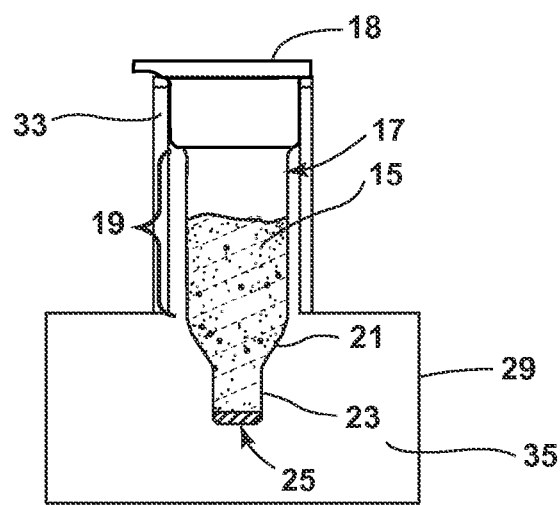
FIG. 3 is a side view of apparatus of FIG. 2 in an assembled state.

The apparatus shown in FIGS. 2 and 3 further includes a waste collection device 29, which may be, for example, in one embodiment, a closed plastic container with an opening 33 at an upper end and shaped to receive and retain the vial 17 in a position where it is disposed above a waste collection portion 35. For this purpose, in one embodiment, the vial 17 has a lip 18 around its upper edge or rim for purposes of resting against the top surface 19 of the waste collection container 29. Such a lip 18 may be positioned elsewhere along the side of the vial 17 in various embodiments.

Further according to the illustrative embodiment, a wash buffer container and releaser capsule 41 is provided, one embodiment of which is illustrated in FIGS. 4 to 7. The illustrative capsule 41 includes a body 43 (FIG. 5), which may be formed of plastic, and which has a hollow cylindrical chamber 45 and first and second grooves 47, 49 formed on its outer circumference 51 positioned respectively near the upper and lower ends of the body 43. First and second o-rings 52, 54 (FIG. 4) respectively reside in the grooves 47, 49.

In one embodiment, the capsule 41 further includes a spike 53 which may be formed of plastic, with an o-ring seal 55. One end of the spike 53 extends into the chamber 64, while the opposite end extends outside the chamber 64 and has a forked tail portion 66. In the illustrative embodiment, the spike 53 further has a pointed tip 56.

In one embodiment, the chamber 64 of the capsule 41 is filled with a wash buffer solution 67 (FIG. 8) and then is sealed; for example, by a thin metal foil 58 applied across the top opening 60. In various embodiments, the wash buffer solution may comprise water, pH buffers, detergents, chelating agents, salts, chaotropic agents, solvents such as ethanol and isopropanol, acids, bases, with optional protease, DNAse or RNAse.

Figure 8:
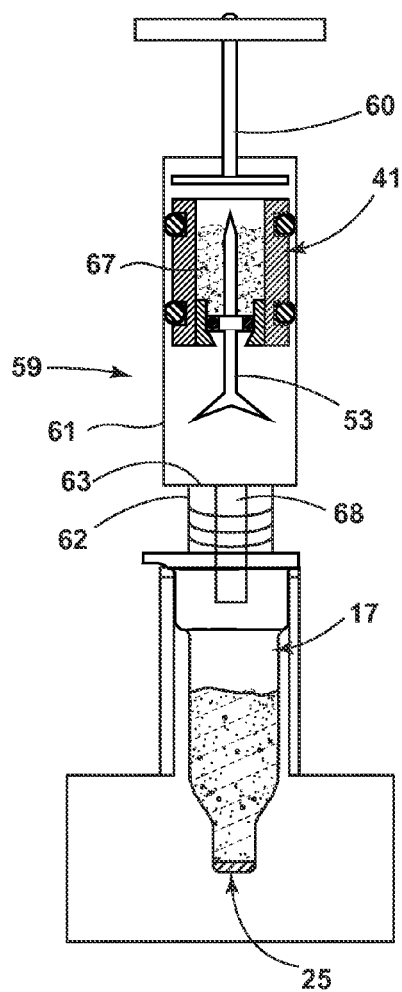
FIG. 8 is a side schematic view illustrating arrangement of a capsule according to FIG. 4 in a syringe cooperating with the apparatus illustrated in FIGS. 2 and 3.

As may be seen with reference to FIG. 8, the capsule 41 is shaped and dimensioned to ride up and down within the barrel 61 of a syringe 59 with the o-rings 52, 54 sealably engaged with the interior side surface of the barrel 61 of the syringe 59. In one embodiment, the end 62 of syringe 59 threads into the top of the vial 17. In the illustrative embodiment, the seal provided by the o-rings 52, 54 is an airtight seal such that when the plunger or drive piston 60 of the syringe 59 is activated to push the capsule 41 downwardly, air (pneumatic) pressure acts to push or force all of the liquid in the vial 17 out through the membrane 25 and into the waste collection container 29.

Figure 8A:
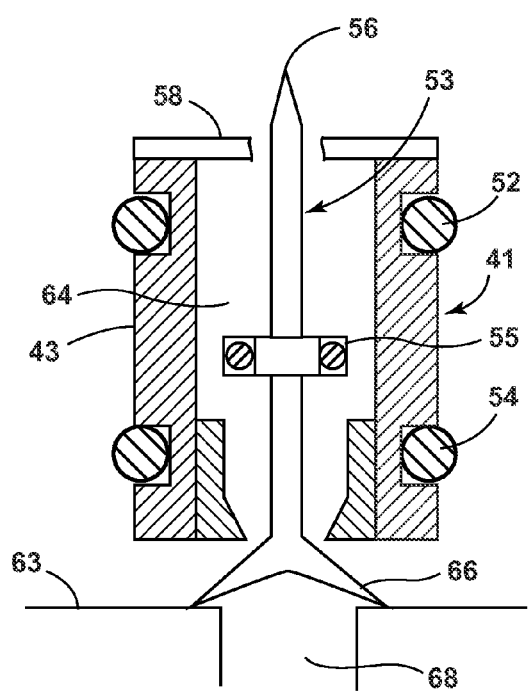
FIG. 8A is a side sectional view illustrating the capsule of FIG. 4 in a wash buffer release position.

As the plunger 60 of the syringe 59 proceeds further downwardly, the forked tail 66 of the spike 53 of the capsule 41 comes into contact or abutment with a portion of the inner bottom edge 63 of the syringe 59, stopping movement of the spike 53 and its o-ring 55 and causing the spike 53 to pierce the seal 58 across the top of the capsule 41, as shown in FIG. 8A. This piercing of the seal 58 releases the wash buffer solution 67, which then is forced by the plunger 60 into the opening 68 in the end or tip of the syringe 59 and then through the membrane 25. As the wash buffer solution 67 passes through the membrane 25, it washes the nucleic acid held by the membrane 25, such that substantially pure nucleic acid is now held by the membrane 25.

Figure 9:
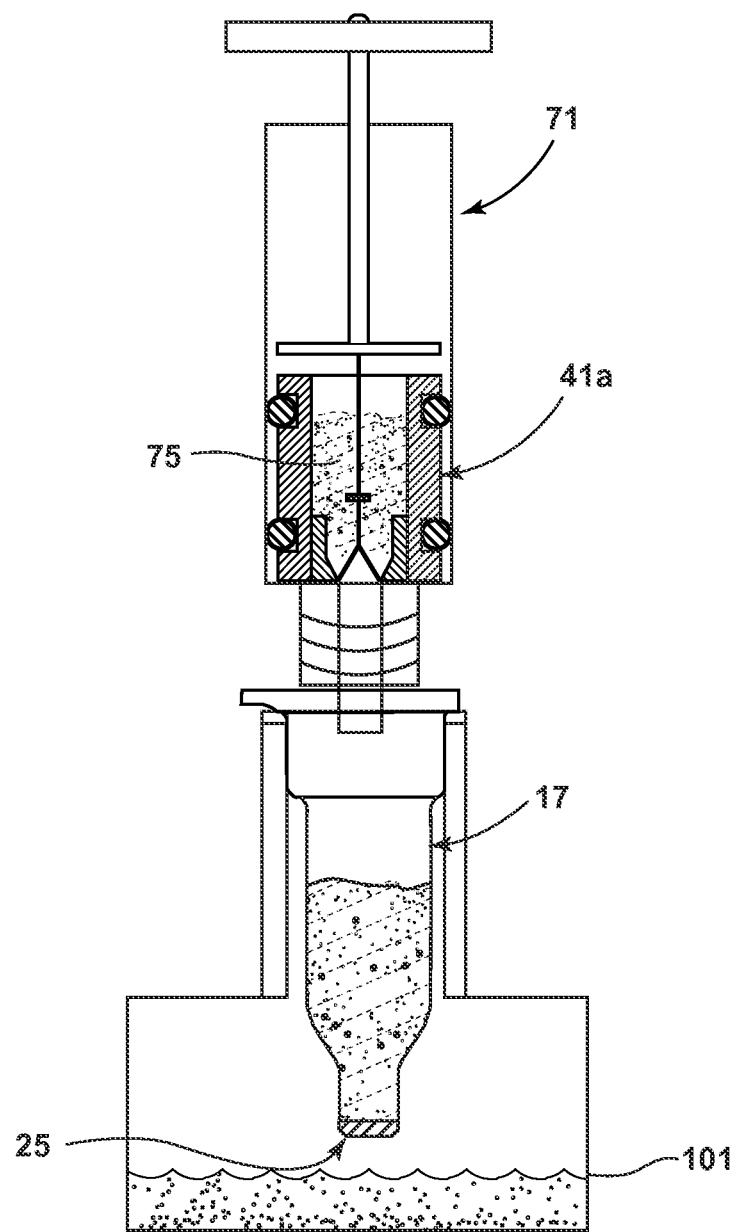
FIG. 9 illustrates a process employing a second syringe to achieve pure nucleic acid.

As shown in FIG. 9, a second syringe 71 containing a capsule 41a constructed like capsule 41 of FIGS. 4-7, may then be screwed into or otherwise sealably attached to the vial 17 and used to further wash the pure nucleic acid with a solution 75 to elute or flush off a selected nucleic acid into a second vessel or tube 101. In one embodiment, if it is desired to release the bound DNA, RNA or other nucleic acids from the membrane a final wash may comprise water or buffers for pH control with optional additives to prevent or retard nucleic acid degradation, such as chelating agents, as known in the art.

It may be noted that various "spin-column" commercial kits can be adapted to work with apparatus as disclosed herein, such kits employing spin-columns which are based on silica or similar absorption techniques. One example are the spin-column RNA/DNA purification kits available from Quiagen N.V. of The Netherlands, which can provide one formulation of a nucleic acid preparation solution 14, a wash buffer 67 and an elution solution 75. Other manufacturers of such kits include Zymo Research, Invitrogen/Life Sciences, Bio-Rad, Thermo Scientific, and Promega.

Apparatus according to the illustrative embodiments can be paired up with other techniques for rapid DNA/RNA detection, such as disease diagnostics or laboratory work/ screening.

The rapid nucleic acid extraction apparatus illustrated in FIGS. 1-14 may form the first step in a series of steps. Firstly, DNA/RNA is extracted using the rapid nucleic acid extraction device. Next, a volume of purified nucleic acid is transferred using a pipetting device, or any other suitable liquid transfer method, etc., to a tube containing a cocktail of enzymes, primers, dNTPs, salts, buffer and water. The sample is then subjected to a predetermined set of thermocycling conditions or other amplification strategies such as Loop-mediated isothermal amplification (LAMP). Finally, the contents of the tube can be subjected to analysis to determine whether a target DNA or RNA is present.

The thermocycling can also be made field portable by using "hand-held PCR machines" or similar. For field use, the cocktail of enzymes, primers, etc. are tuned for each target. Such tuning may heavily depend on know-how and experience to optimize the process. The final detection again, can also be made field portable.

For Ebola and other RNA viruses/targets, a reverse-transcription PCR can be performed. Again, success is highly dependent on the optimizations prior to production, and can be made robust enough for field use by personnel not trained in the biological sciences.

While the illustrative embodiments provide convenient and readily useable devices with relatively low part count, other embodiments can be provided wherein a series of syringes are employed. For example, a first syringe applies pneumatic air pressure to force a nucleic acid solution through a membrane 25, a second syringe is then be used to wash the membrane 25 with a wash buffer such as wash buffer 67 (See FIGS. 4, 8); a third syringe next applies pneumatic air pressure, a fourth syringe next applies the elution/buffer/water solution, e.g., 75 of FIG. 9, with a fifth syringe applying a final pneumatic air "wash." In other embodiments, a capsule may be installed in a closed tube, as opposed to a syringe, and air pressure may be applied through a port in the tube beneath the capsule to force a nucleic acid solution, e.g. 15, through a membrane. A vacuum may thereafter be applied to the port beneath the capsule to pull the capsule downwardly so as to activate a rupturing mechanism and release a wash buffer, e.g. 67.

The capsules, e.g., 41, can be sealed on one or both ends to contain preloaded contents. The capsules can also be sealed only on one side to allow loading of contents from the open end. Various embodiments may involve the use of multiple capsules together or in sequence depending on requirement or application. While the cross-sections of syringes and capsules of the illustrative embodiments have been disclosed as being circular, it should be understood that other cross-sectional geometries, such as, e.g., square, rectangular, or elliptical may be used in other embodiments.

Figure 11:
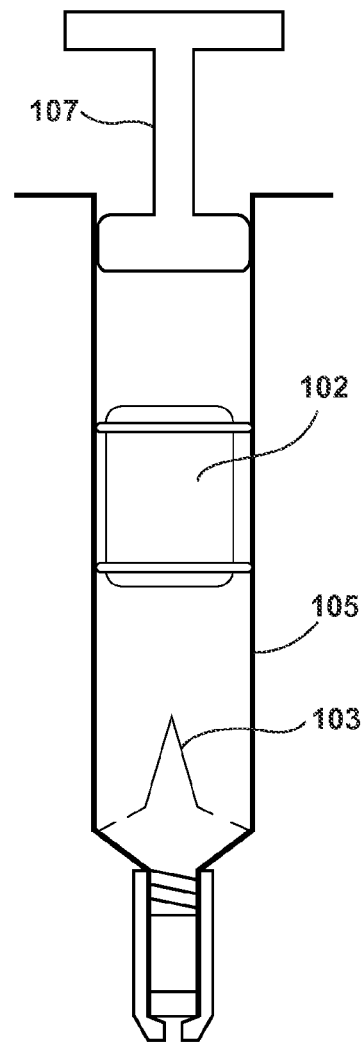
FIG. 11 illustrates an alternative capsule and capsule rupturing mechanism.
Figure 12:
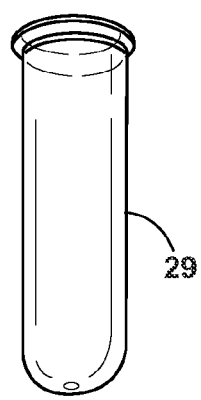
FIG. 12 illustrates one embodiment of a waste collection receptacle.
Figure 13:
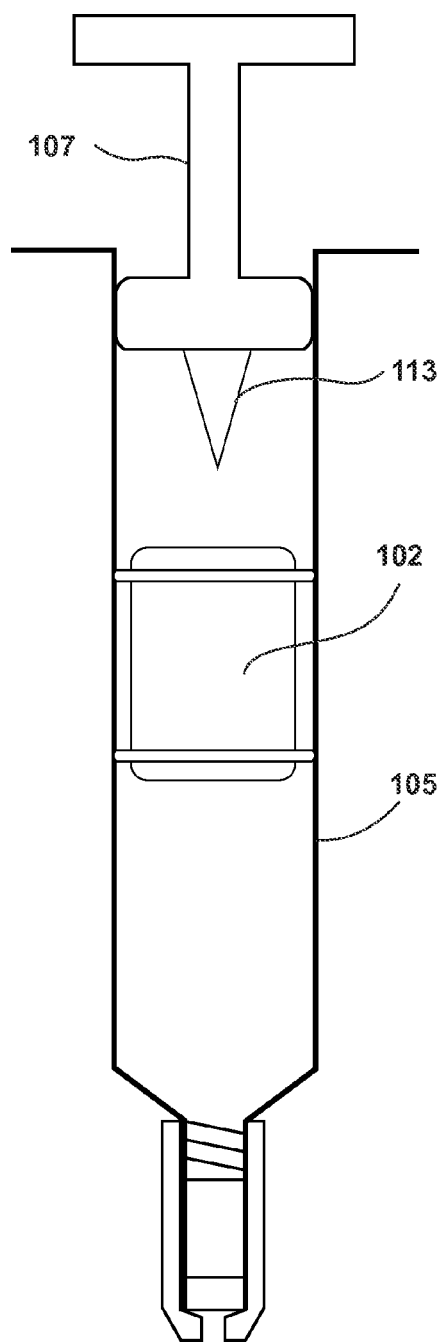
FIG. 13 is a side schematic view of an alternate embodiment.
Figure 14:
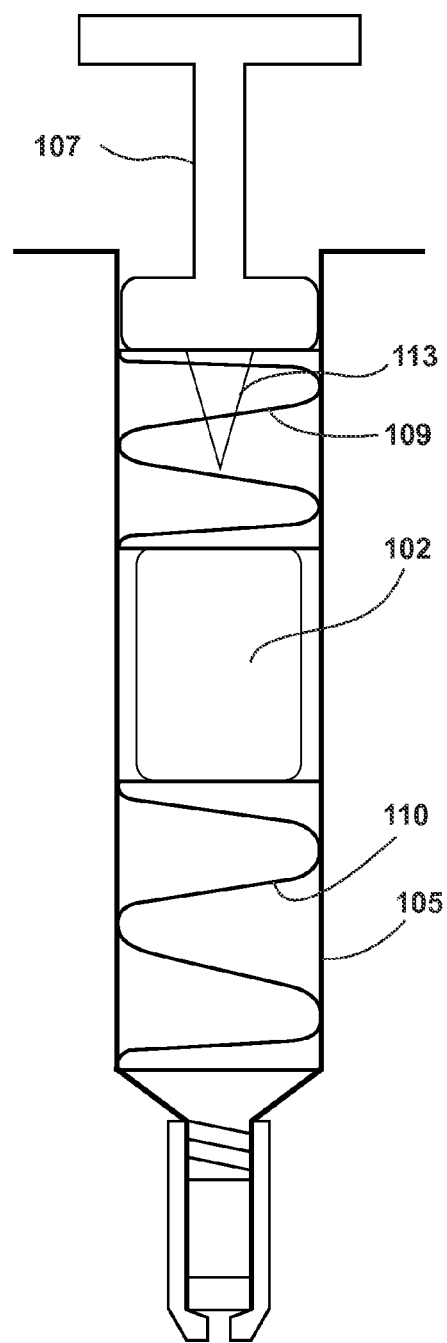
FIG. 14 is a side schematic view of another alternate embodiment.

As illustrated in FIGS. 11 and 13-14, capsule release shafts or spikes, e.g. 103, 113 for releasing the contents of a capsule, e.g. 102, can also be installed near the end of a syringe barrel 105 or on the plunger 107 itself and then driven downwards to puncture or rupture a capsule 102.

Figure 10:
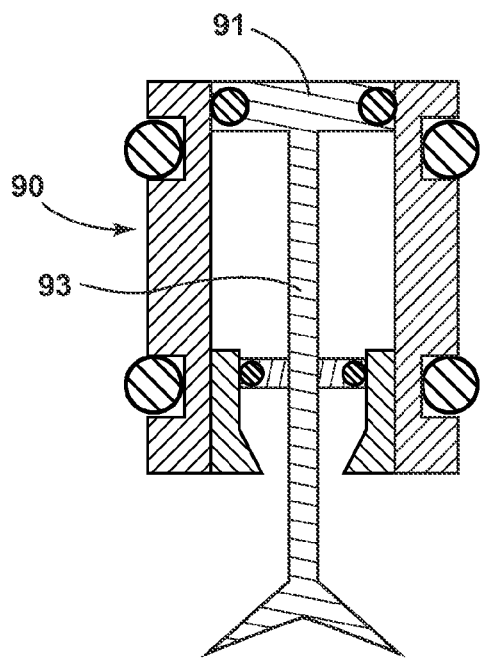
FIG. 10 is a side sectional view of an alternative capsule embodiment.

Capsule orientation can also be inverted such that the spike, e.g. 53 is at the top facing the plunger, e.g. 60, with the piercing end 55 facing down towards the bottom of the syringe. FIG. 10 illustrates another capsule embodiment 90 where the capsule is closed by a disc or plug 91 attached to the top of a shaft 93, with the other components of the capsule being constructed in accordance with FIGS. 4-7.

The o-rings employed in illustrative embodiments can be replaced with dynamic seal techniques such as soft plastic ridges, or alternatively replaced by the use of springs, e.g. 109, 110 (FIG. 14) before and after the capsule, for controlling capsule positioning and capsule release timings.

Thus, those skilled in the art will appreciate that various adaptations and modifications of the just described preferred embodiment can be configured without departing from the scope and spirit of the invention. Therefore, it is to be understood that, within the scope of the appended claims, the invention may be practiced other than as specifically described herein.

What is claimed is:

1. A nucleic acid extraction apparatus comprising:
   a container containing a solution comprising nucleic acid and undesired components, the container further comprising a membrane configured to capture nucleic acid;
   a rupturable capsule containing a wash buffer;
   a rupturing element for rupturing said capsule so as to release said wash buffer;
   a syringe device, said rupturable capsule being positioned within said syringe device, above a lower end of said syringe device and beneath a plunger of said syringe device, the lower end of said syringe device being shaped to fit into an open end of said container comprising a solution of nucleic acid and undesired components;
   the plunger of said syringe device being depressible so as to first force said solution comprising nucleic acid and undesired components through said membrane configured to capture nucleic acid such that the membrane retains nucleic acid while passing the undesired components of the solution therethrough; and
   wherein said plunger is further depressible so as to cause said rupturing element to rupture said rupturable capsule and release said wash buffer and to thereafter drive said wash buffer out of the lower end of said syringe device and through said membrane configured to capture nucleic acid, thereby leaving pure nucleic acid on said membrane.

2. The apparatus of claim 1 wherein pneumatic pressure generated by depression of said plunger forces said solution through said membrane.

3. The apparatus of claim 1 further comprising a second syringe apparatus configured to further wash said membrane to elute a selected nucleic acid.

4. The apparatus of claim 3 wherein the selected nucleic acid comprises one of: RNA, DNA, cDNA, cRNA, modified DNA, modified RNA, tRNA, rRNA, tmRNA, PNA, LNA, GNA, or TNA.

5. The apparatus of claim 1 wherein said rupturable capsule comprises a solid body component with a hollow interior and a material attached to said solid hollow body component which is rupturable by said rupturing element to release said wash buffer.

6. The apparatus of claim 5 wherein said material is a metal foil and wherein said rupturing element is configured to pierce said metal foil to release said wash buffer.

7. The apparatus of claim 1 wherein said capsule has a sealing mechanism which defines first and second chambers within the syringe device such that movement of said plunger downwardly causes downward movement of said capsule within said syringe device.

8. The apparatus of claim 1 comprising one or more springs located within said syringe configured to control positioning of said capsule and the time of release of said wash buffer.

9. The apparatus of claim 5 further comprising first and second springs located within said syringe and configured to control positioning of said capsule and the time of release of said wash buffer.

10. Nucleic acid extraction apparatus comprising:
    a first container configured to receive a nucleic acid solution ready for extraction and having a membrane located at a lower end thereof, said membrane being configured to capture nucleic acid while passing other components of the solution;
    a capsule containing a buffer solution having a top opening and having a rupturable seal across said top opening;
    a syringe insertable into an open top end of said first container, the syringe containing said capsule containing a buffer solution, said capsule containing a buffer solution being moveable downwardly within said syringe in response to activation of a plunger of the syringe;
    a spike for rupturing said seal; and
    wherein the capsule containing a buffer solution is so configured and positioned within the syringe that, after said syringe is inserted into said container, downward movement of the capsule within the syringe first forces the nucleic acid solution in the first container through the membrane configured to capture nucleic acid, after which the spike ruptures said seal, thereby releasing said buffer solution into said first container.

11. The nucleic acid extraction apparatus of claim 10 further configured such that further downward movement of the plunger of said syringe forces said buffer solution through said membrane thereby resulting in pure nucleic acid residing on the membrane.

12. The nucleic acid extraction apparatus of claim 10 further comprising a second syringe apparatus configured to further wash said membrane to elute a selected nucleic acid.

13. The nucleic acid extraction apparatus of claim 12 wherein the selected nucleic acid comprises one of: RNA, DNA, cDNA, cRNA, modified DNA, modified RNA, tRNA, rRNA, tmRNA, PNA, LNA, GNA, or TNA.

14. The apparatus of claim 10 wherein said rupturable capsule comprises a solid body component with a hollow interior and a material attached to said solid hollow body component which is rupturable by said rupturing element to release said wash buffer.

15. The apparatus of claim 14 wherein said material is a metal foil and wherein said rupturing element is configured to pierce said metal foil to release said wash buffer.

16. The apparatus of claim 10 wherein said capsule has a sealing mechanism which defines first and second chambers within the syringe device such that movement of said plunger downwardly causes downward movement of said capsule within a barrel of said plunger.

* * * * *